(12) United States Patent
Ichinose et al.

(10) Patent No.: US 8,045,166 B2
(45) Date of Patent: Oct. 25, 2011

(54) METHOD OF PARTICLE DETECTION, APPARATUS THEREFOR, METHOD OF FORMING PARTICLE CONCENTRATION DIFFERENCE IN DISPERSION LIQUID, AND APPARATUS THEREFOR

(75) Inventors: Nobuyuki Ichinose, Kyoto (JP); Yoshiyuki Nonoguchi, Kyoto (JP); Toshihiro Nakayama, Kyoto (JP)

(73) Assignee: National University Corporation Kyoto Institute Of Technology, Kyoto (JP)

( * ) Notice: Subject to any disclaimer, the term of this patent is extended or adjusted under 35 U.S.C. 154(b) by 375 days.

(21) Appl. No.: 12/300,279

(22) PCT Filed: May 2, 2007

(86) PCT No.: PCT/JP2007/059385
§ 371 (c)(1),
(2), (4) Date: Nov. 10, 2008

(87) PCT Pub. No.: WO2007/129667
PCT Pub. Date: Nov. 15, 2007

(65) Prior Publication Data
US 2009/0180121 A1    Jul. 16, 2009

(30) Foreign Application Priority Data
May 10, 2006  (JP) ................. 2006 131983

(51) Int. Cl.
*G01N 21/00* (2006.01)
(52) U.S. Cl. ..................... 356/441; 356/436
(58) Field of Classification Search .......... 356/432–444, 356/409–415
See application file for complete search history.

(56) References Cited

FOREIGN PATENT DOCUMENTS

| | | | |
|---|---|---|---|
| JP | 5296914 | A | 11/1993 |
| JP | 2003210159 | A | 7/2003 |
| JP | 2003344260 | A | 12/2003 |
| JP | 2005144538 | A | 6/2005 |
| JP | 2005168495 | A | 6/2005 |
| JP | 2005287419 | A | 10/2005 |
| JP | 2005335020 | A | 12/2005 |
| WO | WO 03/062867 | A2 | 7/2003 |
| WO | PCT/JP2007/059385 | | 7/2007 |

OTHER PUBLICATIONS

Kaustubh R. Rau et al., Investigation of laser-induced cell lysis using time-resolved imaging, journal: Applied Physics Letters, Apr. 12, 2004, pp. 2940-2942, vol. 84, No. 15, American Institute of Physics.

Y. Hosokawa et al., Nondestructive isolation of single cultured animal cells by femtosecond laser-induced shockwave, journal: Applied Physics: Materials Science & Processing, 2004, pp. 795-798, vol. A, No. 79.

*Primary Examiner* — Gregory J. Toatley, Jr.
*Assistant Examiner* — Tri T Ton
(74) *Attorney, Agent, or Firm* — Ditthavong Mori & Steiner, P.C.

(57) ABSTRACT

A method of particle detection includes a shock wave generating step of irradiating a dispersion liquid having dispersed first particles having a first diameter and second particles having a second diameter larger than the first diameter, with a pulse laser, and generating a shock wave in the dispersion liquid, a migration speed difference imparting step of migrating and accelerating the first particles at a first acceleration speed, and the second particles at a second acceleration speed higher than the first acceleration speed, by the shock wave generated at the shock wave generating step, and a detecting step of detecting the first or second particles.

11 Claims, 5 Drawing Sheets

METHOD OF PARTICLE DETECTION, APPARATUS THEREFOR, METHOD OF FORMING PARTICLE CONCENTRATION DIFFERENCE IN DISPERSION LIQUID, AND APPARATUS THEREFOR

TECHNICAL FIELD

The present invention relates to a method of particle detection, an apparatus therefor, a method of forming a particle concentration difference in a dispersion liquid, and an apparatus therefor and more particularly, to a method of particle detection, an apparatus therefor, a method of forming a particle concentration difference in a dispersion liquid, and an apparatus therefor, regarding first and second particles having different diameters.

BACKGROUND ART

The manipulation and process of a microscopic object has been especially focused on recently relative to nanotechnology and biotechnology. The microscopic object of the order of micrometers can be manipulated under a microscope by a laser beam without being touched by use of a laser tweezers, and it can be processed by laser ablation and a polymerization reaction of the laser. However, it is difficult to bring the microscopic object and another object together or to inject another object into the microscopic object even by combining the above techniques. Since a shock wave (laser-induced shock wave) generated by focusing the laser beam in a liquid by an objective lens of a microscope can highly accelerate the object, it is regarded as effective energy to perform an operation requiring high energy.

Here, techniques regarding the above are disclosed in Japanese Unexamined Patent Publication No. 2003-210159, Japanese Unexamined Patent Publication No. 2003-344260, Japanese Unexamined Patent Publication No. 2005-144538, Japanese Unexamined Patent Publication No. 2005-335020, Japanese Unexamined Patent Publication No. 2005-287419, Japanese Unexamined Patent Publication No. 2005-168495, and Appl. Phys. Lett., 84, 2940 (2004), Appl. Phys. A, 79, 795 (2004).

While a method of accelerating particles in a uniform solution to form a concentration difference includes an electrophoresis method and an dielectrophoresis method, only ion having a charge can be migrated in the electrophoresis method. According to the above electrophoresis method, since a migration speed is low, the problem is that it takes time for analysis. In addition, chromatography using absorption and permeation or distribution equilibrium is a method of migrating an object to form a concentration difference and this method is widely used as a separation and analysis method of a mixture. Meanwhile, an ultracentrifugal separation method is applied to a high molecular weight molecule and used to measure and separate the molecules. However, since both of them include diffusion and migration of the object in principle, it is difficult to implement both high resolution and high speed or miniaturization.

More specifically, according to the conventional electrophoresis method and the dielectrophoresis method, the problem is that the target is limited to the ion having the charge and the migration speed is low. In addition, according to the conventional chromatography and the centrifugal separation method, the problem is that it is difficult to implement both high resolution and high speed or miniaturization.

Here, many researchers generate shock waves by focusing the pulse laser into the liquid with the microscope, and study its generation mechanism (Appl. Phys. Lett., 84, 2940 (2004), Appl. Phys. A, 79, 795 (2004)). The well known techniques using the laser-induced shock wave include separation of a cell and a part of the cell (Japanese Unexamined Patent Publication No. 2003-210159), acceleration and migration of particles (Appl. Phys. A, 79, 795 (2004)), control of a particle traveling direction (Japanese Unexamined Patent Publication No. 2003-344260), and process of a microscopic object (Japanese Unexamined Patent Publication No. 2005-144538 and Japanese Unexamined Patent Publication No. 2005-335020). The accelerated particle includes a particle such as a gold colloid and a high molecular latex particle having a size of order of nanometers to micrometers, and a live cell. Thus, by use of the acceleration of the particles, marking is performed with the intention of enhanced Raman spectroscopy in the cell by the injection into the cell under the microscope. According to the present invention, it has been found that the target to be accelerated can range from a low molecule to a high molecule, so that a function depending on the molecule can be applied and a molecular size can be analyzed. In addition, a laser injection method for injecting an extracellular object into a cell with the laser-induced shock wave is proposed (in Japanese Unexamined Patent Publication No. 2005-287419, and Japanese Unexamined Patent Publication No. 2005-168495).

Thus, according to the above Japanese Unexamined Patent Publication No. 2003-210159, Japanese Unexamined Patent Publication No. 2003-344260, Japanese Unexamined Patent Publication No. 2005-144538, Japanese Unexamined Patent Publication No. 2005-335020, Japanese Unexamined Patent Publication No. 2005-287419, Japanese Unexamined Patent Publication No. 2005-168495, and Appl. Phys. Lett., 84, 2940 (2004), Appl. Phys. A, 79, 795 (2004), they are techniques related to the process and the cell injection limited to the specific particle and cell, and cannot cope with the case where the first and second particles having the different diameters exist in the dispersion liquid.

DISCLOSURE OF THE INVENTION

According to the present invention, a relatively large particles dispersed in a dispersion liquid are accelerated by a laser-induced shock wave at high speed, and a concentration difference can be imparted to the particles in the dispersion liquid, and the principle of chromatography (laser permeation chromatography) by a pulse laser is provided. In addition, an apparatus for performing the above process for measurement and separation is within the scope of the present invention.

It is an object of the present invention to provide a method of particle detection capable of easily detecting particles in a dispersion liquid in a short time.

It is another object of the present invention to provide an apparatus for particle detection capable of easily detecting particles in a dispersion liquid in a short time.

It is still another object of the present invention to provide a method of forming a particle concentration difference in a dispersion liquid capable of being performed easily in a short time.

It is still another object of the present invention to provide an apparatus for forming a particle concentration difference in a dispersion liquid capable of being performed easily in a short time.

In addition, the concentration difference here includes not only the gradual concentration increase or decrease of the predetermined particles from a first region toward a second region different from the first region, but also the concentration gradient in which the concentration of the predetermined particles is increased or decreased stepwise, and also the one formed by relatively dividing into a part having the high concentration of the predetermined particles and a part having the low concentration of the predetermined particles. Here, the concentration difference includes a spatial concentration difference, that is, a three-dimensional concentration difference.

A method of particle detection according to the present invention includes a shock wave generating step of irradiating a dispersion liquid having dispersed first particles having a first diameter and second particles having a second diameter larger than the first diameter, with a pulse laser, and generating a shock wave in the dispersion liquid, a migration speed difference imparting step of migrating and accelerating the first particles at a first acceleration speed, and the second particles at a second acceleration speed higher than the first acceleration speed, by the shock wave generated at the shock wave generating step, and a detecting step of detecting the first or second particles.

The above method of particle detection can detect the particles by accelerating the first and second particles having the different diameters and dispersed in the dispersion liquid by the laser-induced shock wave, and forming a part having the high concentration of the accelerated particles. According to the laser-induced shock wave, the particles can be accelerated in a short time, and the particle can be accelerated and migrated based on the diameter. In addition, the laser-induced shock wave can be easily generated in the dispersion liquid by use of the pulse laser. Thus, the particle in the dispersion liquid can be easily detected in a short time.

In addition, the particle in this specification includes a molecular assembly such as cholesterol particles, and a molecule in a solution. In addition, the particle detection in this specification includes the detection of the particles to measure and separate the particles. In addition, the present invention includes a case where a part or all of the particles are dissolved. In addition, the diameter of the particle is calculated based on a hydrodynamic radius. Here, the first acceleration speed includes zero and only the second particle may be accelerated and migrated.

Preferably, the detecting step is a step of detecting a refractive index, absorption degree, or fluorescent intensity of the particle.

Further preferably, the second particles have a radius of 1 nm or more.

According to another aspect of the present invention, an apparatus for particle detection includes pulse laser generating unit for generating a pulse laser, shock wave generating unit for generating a shock wave in a dispersion liquid having dispersed first particles having a first diameter and second particles having a second diameter larger than the first diameter, with the pulse laser generated by the pulse laser generating unit, migration speed difference imparting unit for migrating and accelerating the first particles at a first acceleration speed, and the second particles at a second acceleration speed higher than the first acceleration speed, by the shock wave generated by the shock wave generating unit, and detecting unit for detecting the first or second shock waves accelerated and migrated by the migration speed difference imparting unit.

The apparatus for particle detection can detect the particles by accelerating the first and second particles having the different diameters and dispersed in the dispersion liquid by the laser-induced shock wave, and forming a part having the high concentration of the accelerated particles. Thus, the particles in the dispersion liquid can be easily detected in short time.

According still another aspect of the present invention, a method of forming a particle concentration difference in a dispersion liquid includes a shock wave generating step of irradiating a dispersion liquid having dispersed first particles having a first diameter and second particles having a second diameter larger than the first diameter, with a pulse laser and generating a shock wave in the dispersion liquid, and a migration speed difference imparting step of migrating and accelerating the first particles at a first acceleration speed, and the second particles at a second acceleration speed higher than the first acceleration speed, by the shock wave generated at the shock wave generating step.

The method of forming the particle concentration difference in the dispersion liquid can accelerate the first and second particles having the different diameters and dispersed in the dispersion liquid by the laser-induced shock wave, and form a part having high concentration of the accelerated particles. Thus, the particle concentration difference in the dispersion liquid can be easily formed in a short time.

According to still another aspect of the present invention, an apparatus for forming a particle concentration difference in a dispersion liquid includes pulse laser generating unit for generating a pulse laser, shock wave generating unit for generating a shock wave in a dispersion liquid having dispersed first particles having a first diameter and second particles having a second diameter larger than the first diameter with the pulse laser generated by the pulse laser generating unit, and migration speed difference imparting unit for migrating and accelerating the first particles at a first acceleration speed, and the second particles at a second acceleration speed higher than the first acceleration speed, by the shock wave generated by the shock wave generating unit.

The apparatus for forming the particle concentration difference in the dispersion liquid can accelerate the first and second particles having the different diameters and dispersed in the dispersion liquid by the laser-induced shock wave, and form a part having the high concentration of the accelerated particles. Thus, the particle concentration difference in the dispersion liquid can be easily formed in a short time.

In addition, according to the present invention, the permeation gel that is used in the gel permeation chromatography is not required and the solvent can be used as it is. Therefore, the cost can be low. In addition, both high resolution and high speed or miniaturization can be implemented. Furthermore, since the laser-induced shock wave can migrate the relatively large particle, the high molecular weight particle that cannot be introduced due to the cell membrane and the cell wall under normal circumstances can be directly injected into the cell.

BEST MODE FOR CARRYING OUT THE INVENTION

Embodiments of the present invention will be described with reference to the drawings hereinafter. First, a description will be made of a principle. A shock wave can be generated in a dispersion liquid by focusing a laser beam in the dispersion liquid by use of a pulse laser such as a Nd:YAG laser having a Q-switch, a light collection optical system such as a microscope, and water. First particles having a first diameter and second particles having a second diameter larger than the first diameter are dispersed in the dispersion liquid. A change occurring in the dispersion liquid can be measured by any method as long as the absorption, fluorescence, and refractive index can be optically detected and another property change in the dispersion liquid can be detected in a time region from nanoseconds to microseconds at high speed. In addition, an observation position is to be several micrometers to millimeters apart from the focused position. In addition, according to the present invention, it is assumed that particles having a diameter of several nanometers is migrated on a time scale of several nanoseconds.

It is thought that the particles are accelerated hydrodynamically by the propagation of the shock wave generated through light absorption and plasma generation at the focused point. At this time, since the larger particle, that is, the particle having a larger diameter is more accelerated, it is considered that the viscosity at a shock wave front becomes high due to high pressure, and viscosity resistance is generated when the shock wave passes the particles, so that the particle are accelerated. Here, the shock wave front is a front surface of the propagation of the shock wave. In addition, since the particle having a small diameter is not accelerated, it is considered that the elastic collision of the shock wave does not occur. Thus, the difference of the particle size can be identified due to this size dependency. In addition, the propagation speed of the shock wave front is 2000 to 2200 m/s. This speed is higher than a migration speed in the electrophoresis method and the dielectrophoresis method.

Figure 1:
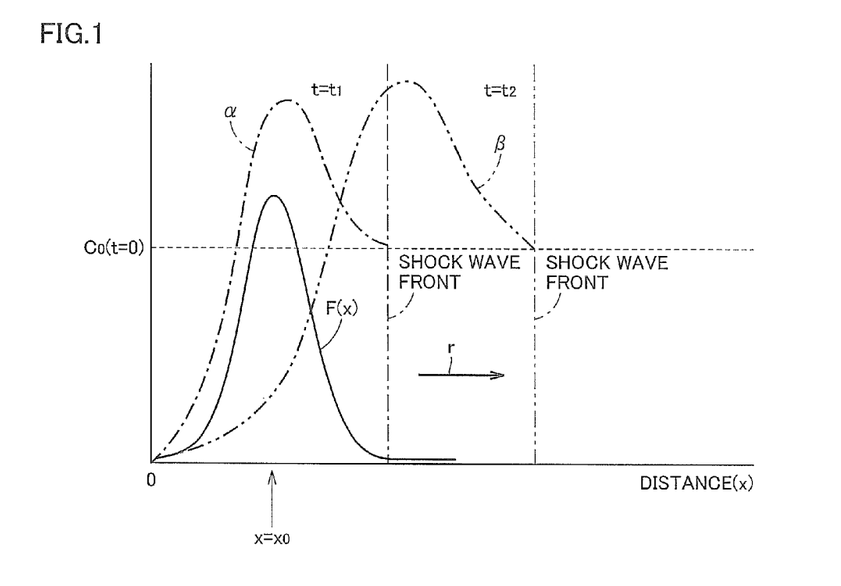
FIG. 1 is a schematic diagram showing a time change of the fluorescent intensity at a position apart from a shock wave generation point based on a concentration distribution change by a laser-induced shock wave.

The principle of the present invention will be described further in detail. Here, a time change of measured fluorescent intensity can be understood as follows. FIG. 1 is a schematic diagram showing a time change of the fluorescent intensity at a focused position ($x_0$) of an observing excitation light source positioned apart from a shock wave generation point based on a concentration distribution change by the laser-induced shock wave. In FIG. 1, a vertical axis designates the concentration of the dispersion liquid, and a horizontal axis designates a distance (x) from the shock wave generation point. In addition, the function shown by a solid line is an observation region function (F(x)) in FIG. 1. Here, the observation region function is a function showing the distribution of the fluorescent intensity in an observation region from a position (x) in an excitation light axis direction centered around the focal position ($x_0$) of the excitation light source when the space distribution of the concentration is monitored by the fluorescence.

Referring to FIG. 1, the concentration distribution in the dispersion liquid is uniform ($C=C_0$) as shown by a dotted line in FIG. 1 before the shock wave is generated (t=0). However, at a time $t=t_1$ after the generation of the shock wave, the concentration distribution is not uniform as shown by the concentration distribution function shown by a one-dot chain line and α. In addition, the position of the shock wave front is shown by a one-dot chain line in FIG. 1. Here, the concentration is low at the shock wave generation point and the concentration is high in the vicinity of the shock wave front. When it is assumed that the distance from the generation point is "x", it is considered that the measured fluorescent intensity is proportional to a formula 1 provided as an integration value of multiplication of the observation region function (F(x)) and the concentration distribution (C (t, x)) at that time with respect to "x"

$$\iint F(x) \cdot C(t,x) dx dt$$ [Formula 1]

Here, the integration range with respect to "t" in FIG. 1 corresponds to an observation gate width. Thus, as shown in FIG. 1, the fluorescent intensity at the time $t=t_1$ becomes higher than that before the shock wave is generated. At a time $t=t_2$ after the generation of the shock wave, the concentration distribution is as shown by a two-dot chain line and β. In addition, the position of the shock wave front is shown by a two-dot chain line in FIG. 1. It can be seen that the fluorescent intensity is lower than that before the shock wave is generated at the time $t=t_2$. In addition, the position of the shock wave front migrates to a position shown by the two-dot chain line in FIG. 1. in a direction shown by γ in FIG. 1. It is considered that the shock wave causes the above concentration change because the shock wave front is high-pressure and high-density fluid, so that the particle receives viscosity resistance force proportional to its radius in the propagation direction. The present invention was made based on the above-described principle.

Figure 2:
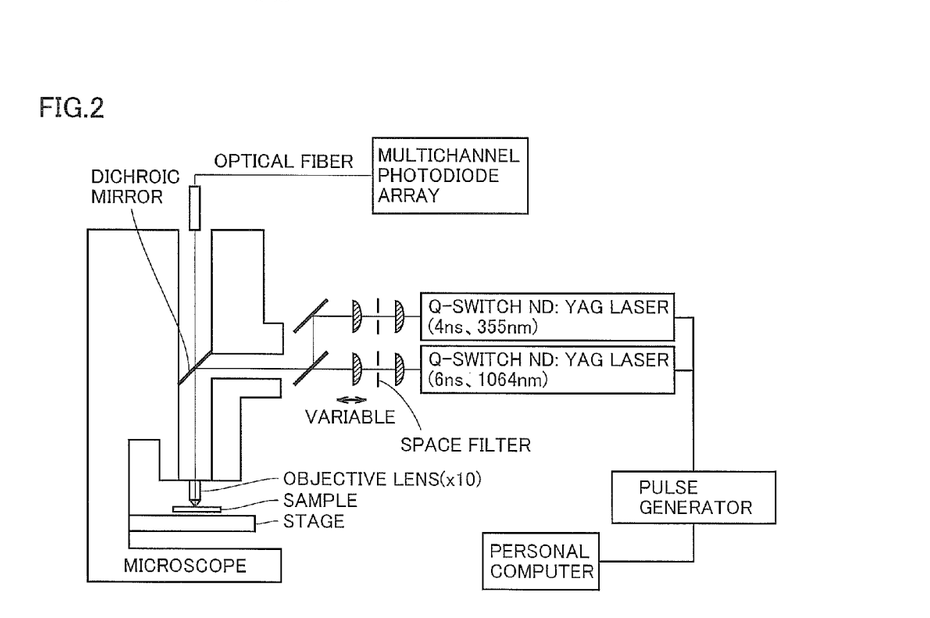
FIG. 2 is a schematic view showing an apparatus.

Next, an apparatus will be described. FIG. 2 is a schematic view showing an apparatus for performing time-resolved fluorescence spectroscopy such that a laser pulse is focused in a dispersion liquid sample under a microscope, as an example of an apparatus of the present invention. This apparatus is characterized in that the pulse laser focused position and the fluoresce observation position in the dispersion liquid can be spatially controlled by adjusting the focused position of an externally provided laser space filter optical system.

Figure 3:
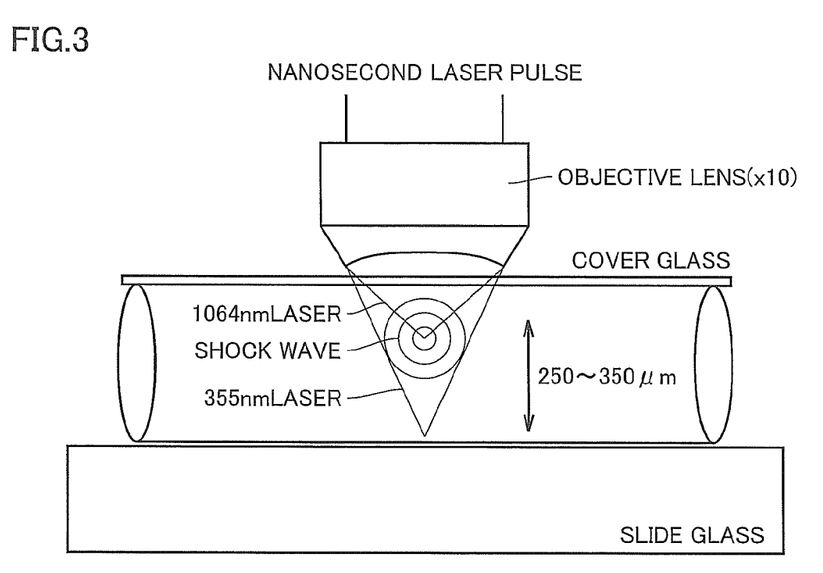
FIG. 3 is a schematic view showing a focused position of a laser beam.

FIG. 3 shows an example of the focused position of a shock wave generation laser (1064 nm pulse laser) and the focused position of a fluoresce observation ultraviolet laser (355 nm pulse laser). In the apparatus shown in FIG. 2, two Nd:YAG lasers are used and their oscillation timings are controlled by a delay circuit in the order of nanoseconds. The focused position of the ultraviolet laser coincides with the focal point of the microscope and the fluorescence generated from it is focused on an optical fiber by an imaging lens provided at an upper part of the microscope and led to a spectrometer. A space resolution in a depth direction is determined by an objective lens magnification and the diameter of the optical fiber and can be selected according to need. In addition, when the microscope is a confocal type, a higher space resolution can be provided.

Here, the dispersion liquid in which the first and second particles are dispersed, is arranged at a region sandwiched by a cover glass and a slide glass as shown in FIG. 3. According to a prepared slide composed of them, a distance between the cover glass and the slide glass can be ensured by interposing an annular resin ring between the cover glass and the slide glass. In addition, the control regarding the above is performed by a control unit (not shown) in a personal computer.

Thus, an apparatus for forming the particle concentration difference in the dispersion liquid according to the present invention includes the Nd:YAG laser and pulse generator for generating the shock wave, as pulse laser generating unit for generating the pulse laser, the microscope containing the objective lens and the optical fiber, as shock wave generating unit for generating the shock wave in the dispersion liquid in which first particles having a first diameter and second particles having a second diameter larger than the first diameter, with the pulse laser generated by the pulse laser generating unit, and the control unit as migration speed difference imparting unit for accelerating and migrating the first particles at a first acceleration speed, and accelerating and migrating the second particles at a second acceleration speed higher than the first acceleration speed, by the shock wave generated by the shock wave generating unit.

In addition, a method of forming a particle concentration difference in a dispersion liquid according to the present invention includes a shock wave generating step of forming the shock wave in the dispersion liquid by irradiating the dispersion liquid in which first particles having a first diameter and second particles having a second diameter larger than the first diameter are dispersed, with the pulse laser, and a migration speed difference imparting step of migrating and accelerating the first particles at a first acceleration speed and migrating and accelerating the second particle at a second acceleration speed higher than the first acceleration speed by the shock wave generated at the shock wave generating step.

According to the above constitution, the first and second particles having the different diameters dispersed in the dispersion liquid are accelerated by the laser-induced shock wave, and a part having a high concentration of the accelerated particles is formed, so that the particles can be detected. According to the laser-induced shock wave, the particles can be accelerated in a short time and the particles can be accelerated and migrated based on the diameter. In addition, the laser-induced shock wave can be easily generated in the dispersion liquid by use of the pulse laser and the like. Therefore, the particle concentration difference in the dispersion liquid can be easily formed in a short time.

In addition, an apparatus for particle detection according to the present invention includes the Nd:YAG laser and pulse generator for generating the shock wave, as pulse laser generating unit for generating the pulse laser, the microscope containing the objective lens and the optical fiber, as shock wave generating unit for generating the shock wave in the dispersion liquid in which first particles having a first diameter and second particles having a second diameter larger than the first diameter, with the pulse laser generated by the pulse laser generating unit, the control unit as migration speed difference imparting unit for accelerating and migrating the first particles at a first acceleration speed, and accelerating and migrating the second particles at a second acceleration speed higher than the first acceleration speed, by the shock wave generated by the shock wave generating unit, and the Nd:YAG laser and pulse generator for measuring fluoresce, as detecting unit for detecting the first or second particles accelerated and migrated by the migration speed difference imparting unit.

In addition, a method of particle detection according to the present invention includes a shock wave generating step of forming the shock wave in the dispersion liquid by irradiating the dispersion liquid in which first particles having a first diameter and second particles having a second diameter larger than the first diameter are dispersed, with the pulse laser, a migration speed difference imparting step of migrating and accelerating the first particles at a first acceleration speed and migrating and accelerating the second particle at a second acceleration speed higher than the first acceleration speed by the shock wave generated at the shock wave generating step, and a detecting step of detecting the first or second particles.

According to the above constitution, the first and second particles having the different diameters dispersed in the dispersion liquid are accelerated by the laser-induced shock wave, and a part having a high concentration of the accelerated particles is formed, so that the particles can be detected. According to the laser-induced shock wave, the particles can be accelerated in a short time and the particles can be accelerated and migrated based on the diameter. In addition, the laser-induced shock wave can be easily generated in the dispersion liquid by use of the pulse laser and the like. Therefore, the particles in the dispersion liquid can be easily detected in a short time.

In addition, according to the present invention, since permeation gel used in gel permeation chromatography and the like is not needed, the solvent is used as it is. Thus, cost can be low. In addition, both high resolution and high speed or miniaturization can be implemented. In addition, since the laser-induced shock wave can migrate relatively large particles, a high molecular weight particle that cannot be introduced into a cell due to a cell membrane and a cell wall can be directly injected in to the cell by accelerating the particles in the liquid, with the laser.

In addition, the apparatus for forming the particle concentration difference in the dispersion liquid may include separating unit for separating the particles. More specifically, a partition is provided between the accelerated first particles and second particles to separate the first particles and the second particles. Thus, the accelerated first and second particles can be separated in a short time easily.

In addition, although the particles are detected based on the fluorescent intensity of the particles in the above embodiment, the present invention is not limited to this and the particles may be detected based on the reflective index and absorbance value of the particles. Furthermore, the particles may be detected based on another optical detection.

In addition, although the 1064 nm pulse laser is used as the shock wave generation laser in the above embodiment, the laser-induced shock wave may be generated by a pulse laser having a pulse width of nanoseconds or microseconds having another wavelength. In addition, the laser intensity and the distance to the position to generate the laser-induced shock wave can be optionally changed depending on the size of the particles to be accelerated.

In addition, the radius of the second particle is preferably not less than 1 nm, more preferably 1 nm to 1 µm, and further preferably 1 nm to 10 nm. When the radius is more than 1 µm, since the speed is lowered due to the viscosity resistance, the migration speed difference between the first particle and the second particle becomes small, so that it is difficult to form the concentration difference. The size is preferably not more than 10 nm because the effect of reduction in speed due to the viscosity resistance is low. In addition, according to the above constitution, the particle having the radius of 1 nm or more can be accelerated.

Furthermore, the dispersion liquid may contain three or more kinds of particles having different radiuses to be accelerated and migrated respectively in the above constitution.

Figure 4A:
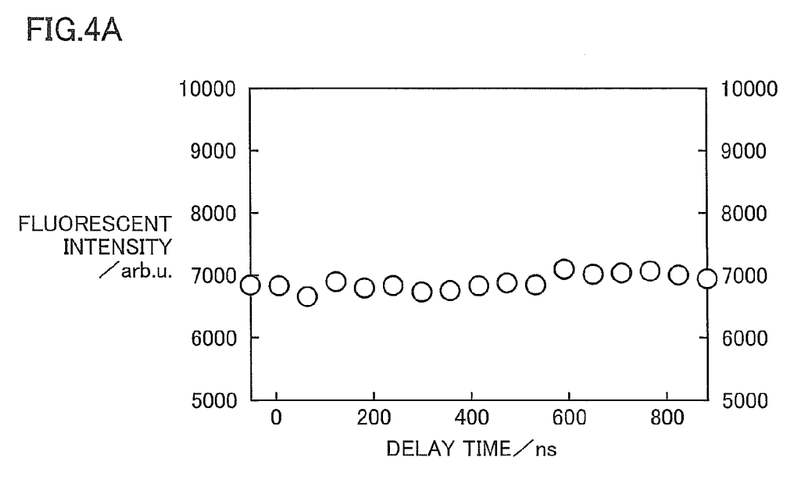
FIG. 4A is a graph showing delay time dependency of a 355 nm fluoresce observing laser pulse on a 1064 nm laser pulse in a case of the fluorescent intensity of pyramine, of the fluorescent intensities of pyranine and pyrene-γ-cyclodextrin 2:2 compound water solution measured by the apparatus shown in FIGS. 2 and 3.
Figure 4B:
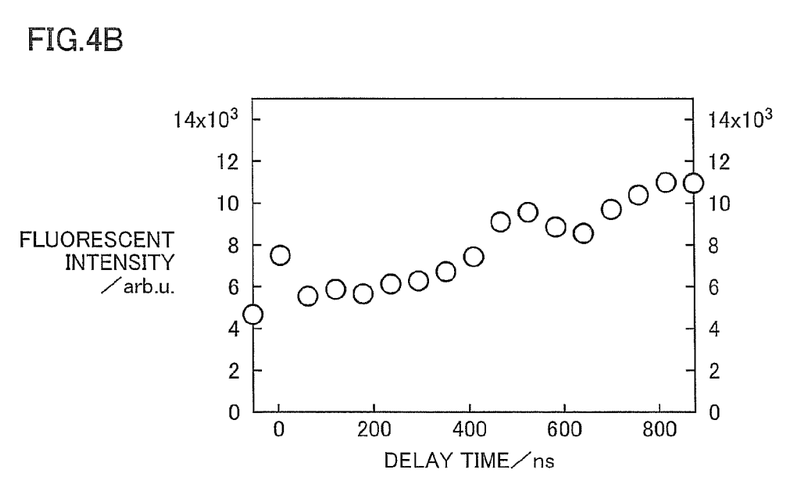
FIG. 4B is a graph showing delay time dependency of the 355 nm fluoresce observing laser pulse on the 1064 nm laser pulse in a case of the fluorescent intensity of pyrene-γ-cyclodextrin 2:2 compound water solution, of the fluorescent intensity of pyranine and pyrene-γ-cyclodextrin 2:2 compound water solution measured by the apparatus shown in FIGS. 2 and 3.

An experiment example will be shown hereinafter. FIGS. 4A and 4B show the delay time dependency of the 355 nm fluoresce observing laser pulse on the 1064 nm laser pulse of the fluorescent intensities of pyranine and pyrene-γ-cyclodextrin 2:2 compound water solution measured by the apparatus shown in FIGS. 2 and 3.

Referring to FIGS. 4A and 4B, the fluorescent intensity of the pyrene-γ-cyclodextrin 2:2 compound at the observed point about 300 μm apart from the focused point after the shock wave is generated by the 1064 nm laser pulse irradiation is increased with time. The arrival time of the shock wave to the observed point is about 200 ns. However, such effect is not achieved in pyranine. This means that the concentration of the pyrene-γ-cyclodextrin 2:2 compound is increased at the observed point. The difference in results of pyranine as the first particles and pyrene-γ-cyclodextrin 2:2 compound as the second particles is a difference in acceleration effect because of their hydrodynamical radiuses of 0.3 nm and 1.0 nm, respectively.

Figure 5:
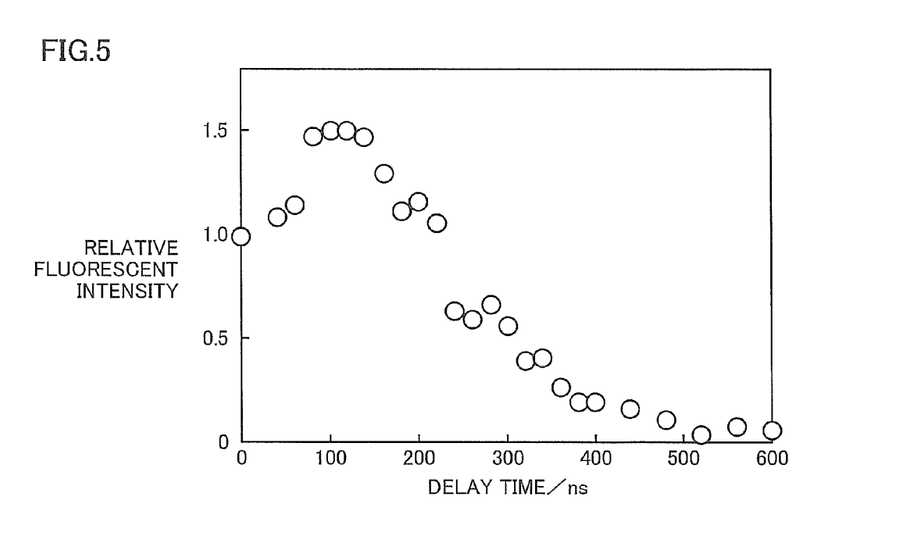
FIG. 5 is a view showing an influence of fluorescence of a mixture solution of ammonium 3-anilino naphthalene-8-sulfonate (referred to as "ANS") and egg albumin (referred to as simply "albumin") by the shock wave.

Another experiment result is shown next. FIG. 5 shows an influence of the fluorescence of the mixed solution of ANS and albumin by the shock wave. In addition, the laser intensity of a fundamental wave to generate the shock wave is 1.7 mJ/pulse, the distance between focal points of the fundamental wave and a third harmonic is 200 μm, and an observation gate width is 50 ns. In addition, the concentration of albumin in a buffer solution is $1.0 \times 10^{-5}$ M, and the concentration of ANS is $3.0 \times 10^{-4}$ M. Here, the diameter of the albumin particle as the second particle is about 4 nm, and the diameter of the ANS particle as the first particle is about 0.6 nm.

Referring to FIG. 5, the buffer solution shows high fluorescence because ANS is taken in albumin. The one in which ANS is taken in albumin is referred to as "albumin-ANS". Although ANS that is not taken in albumin (referred to as "free ANS" hereinafter) shows some fluorescence, its intensity is low. In addition, according to both fluorescences, since the observed wavelengths are different, they can be distinguished. In this case, since ANS is taken in albumin at a ratio of 1:1, it can be thought that the free ANS stays at the same concentration of $2.9 \times 10^{-4}$ M. When this solution is irradiated with the laser shock wave and the fluorescence is observed at a position at a distance of 200 μm, relative intensity of the fluorescence from albumin-ANS to the fluorescence from free ANS is high in the vicinity of the arrival time of the shock wave to the observed point and then reduced thereafter. This shows that the shock wave migrates albumin in the propagation direction and it hardly affects small-sized ANS. Thus, it is shown that the particles can be separated due to the difference in particle diameter.

Figure 6:
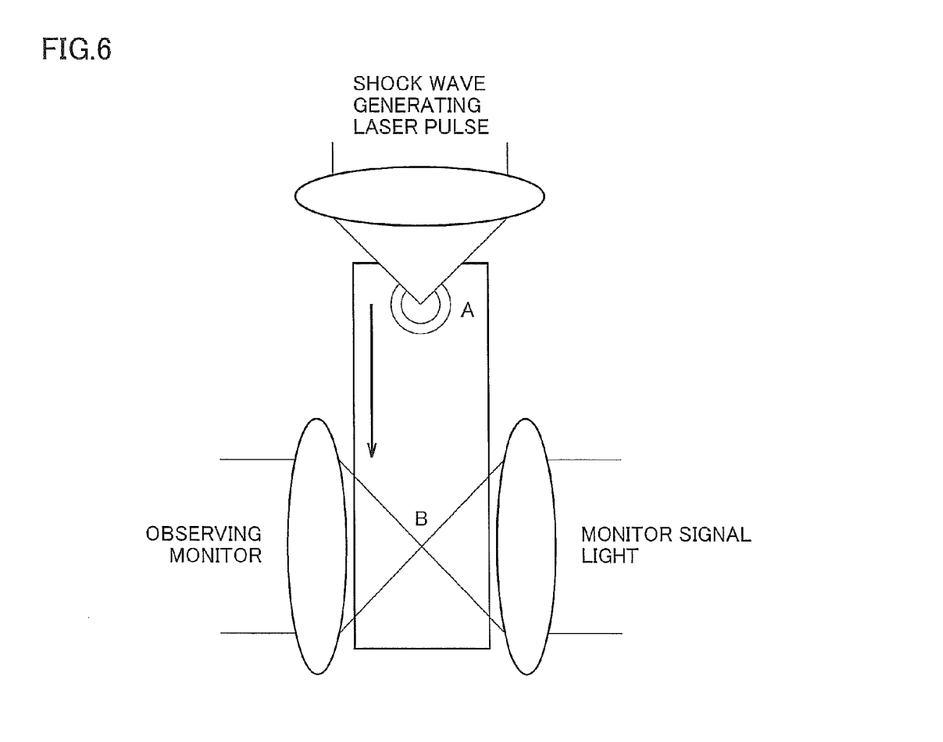
FIG. 6 is a schematic view showing laser permeation chromatography.

Then, an application example will be described. FIG. 6 is a schematic diagram showing laser permeation chromatography. A sample mixture introduced to a point A is accelerated by a shock wave generated by a laser pulse and migrated in a direction of B. At this time, when the hydrodynamic radiuses of the particles in the mixture are different, since the degree of acceleration are different, the particles are spatially separated based on the particle size. Thus, when the solvent flows continuously, the component particles in the mixture and signals corresponding to their amounts are provided at a point B at temporally different timings.

Figure 7:
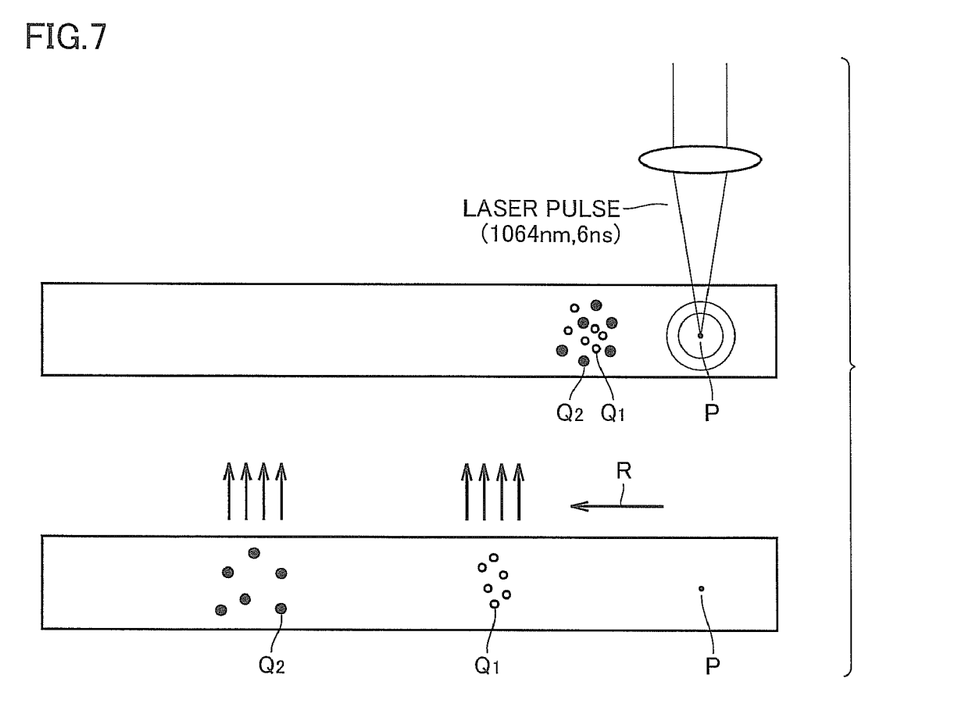
FIG. 7 is a schematic diagram showing a detection apparatus of the particles by the laser permeation chromatography shown in FIG. 6 and showing a position to generate the induced shock wave by the pulse laser and a state of the migrated particles.

This will be described specifically. FIG. 7 is a schematic diagram showing a detection step by the laser permeation chromatography shown in FIG. 6 and showing a position to generate the induced shock wave by the pulse laser and a state of the migrated particles.

Referring to FIGS. 6 and 7, first particles $Q_1$ having a first diameter and second particles $Q_2$ having a diameter larger than the first diameter are dispersed in the dispersion liquid. Here, the shock wave is generated by the pulse laser at a potion shown by a point P. Then, the second particles $Q_2$ having the second diameter is highly accelerated at a second acceleration speed in a direction shown by an arrow R in FIG. 7. Meanwhile, the first particles $Q_1$ having the first diameter smaller than the second diameter is slightly accelerated at a first acceleration speed and observed in the vicinity of the point P that is the shock wave generation point. Here, the fluorescence or scattering to the direction shown by the arrow in FIG. 7 is observed and detected. Thus, they are separately measured.

Although the embodiments of the present invention have been described with reference to the drawings in the above, the present invention is not limited to the above-illustrated embodiments. Various kinds of modifications and variations may be added to the illustrated embodiments within the same or equal scope of the present invention.

INDUSTRIAL APPLICABILITY

The applicable field of the present invention includes the following fields.

* Implementation of High Speed and Miniaturization of the Permeation Chromatography, and Application to Analysis and Sorting Including Molecular Weight Measurement by Use of Size Dependency As an advantageous point in this case, the permeation gel is not needed and the solvent can be used as it is. The permeation part is only a several millimeters long, and acceleration and permeation are performed from the focused part by the several pulses of laser irradiation based on the molecular weight, so that it is considered that the molecular weight measurement (laser permeation chromatography) can be made at super high speed. In addition, in this case, the molecular weight of a molecular complex that cannot be analyzed by the normal gel permeation chromatography can be estimated, and a neutral high molecular weight compound having no charge that cannot be separated by the electrophoresis method can be analyzed. Furthermore, the molecule can be fractionized and sorted by combining a microchannel system.

* Selective Biologic Operation, Marking and Gene Manipulation by Injecting Molecule to Cell The high molecular weight molecule that cannot be introduced due to the cell membrane and the cell wall in general can be directly injected into the cell by acceleration of the molecule in the solution by the laser. In addition, since a low molecular weight medicine and the like can be injected into the cell without any contact by using an inclusion phenomenon, the effect to the living cell can be examined. Similarly, the present invention can be applied to the process of a prepared microcapsule that resembles the cell, and the start of the reaction in the microcapsule by catalyst injection.

Although the range of the molecules that can be accelerated are limited by the hydrodynamic radius in the present invention, the charge of the molecule that is required in the electrophoresis method is not required. Therefore, the present invention can be applied to analysis of nonelectrolyte biologic molecule such as sugar. That is, as for the single molecule, the one having higher molecular weight is highly accelerated due to the molecular size dependency. Therefore, although the molecule having a low molecular weight cannot be accelerated as it is, the low molecule can be accelerated by use of inclusion. For example, the low molecule can be accelerated by use of inclusion with cyclodextrin and calixarene and the like, and by forming high molecule-low molecule complex. In addition, the assembly of low molecule such as micelle, vesicle, assembly of pigment and fine crystal can be accelerated.

The invention claimed is:

1. A method of particle detection comprising:
   a shock wave generating step of activating a shock wave generating unit to irradiate a dispersion liquid having dispersed first particles having a first diameter and second particles having a second diameter larger than said first diameter, with a pulse laser and generating a shock wave in said dispersion liquid;
   a migration speed difference imparting step of applying a migration speed difference imparting unit to migrate and accelerate said first particles at a first acceleration speed, and said second particles at a second acceleration speed higher than said first acceleration speed, by the shock wave generated at said shock wave generating step; and
   a detecting step of detecting said first or second particles in a detection unit.

2. The method of particle detection according to claim 1, wherein
   said detecting step is a step of detecting a refractive index, absorption degree, or fluorescent intensity of the particle.

3. The method of particle detection according to claim 1, wherein said second particles have a radius of 1 nm to 1 μm.

4. An apparatus for particle detection comprising:
   first pulse laser generating unit for generating a pulse laser having a predetermined wavelength;
   second pulse laser generating unit for generating a pulse laser having a wavelength different from said predetermined wavelength;
   shock wave generating unit for generating a shock wave at a predetermined focused position in a dispersion liquid having dispersed first particles having a first diameter and second particles having a second diameter larger than said first diameter, with said pulse laser generated by said pulse laser generating unit;
   migration speed difference imparting unit for migrating and accelerating said first particles at a first acceleration speed, and said second particles at a second acceleration speed higher than said first acceleration speed, by the shock wave generated by said shock wave generating unit; and
   detecting unit for detecting said first or second particles passing through a predetermined observation position in said dispersion liquid positioned apart from said predetermined focused position, at different acceleration speeds generated by said shock wave generated at said focused position, with said pulse laser generated by said second pulse laser generating unit.

5. A method of forming a particle concentration difference in a dispersion liquid, comprising:
   a shock wave generating step of activating a shock wave generating unit to irradiate a dispersion liquid having dispersed first particles having a first diameter and second particles having a second diameter larger than said first diameter, with a pulse laser and generating a shock wave in said dispersion liquid;
   a migration speed difference imparting step of applying a migration speed difference imparting unit to migrate and accelerate said first particles at a first acceleration speed, and said second particles at a second acceleration speed higher than said first acceleration speed, by the shock wave generated at said shock wave generating step; and
   a separating step of separating the first particles and the second particles accelerated and migrated by said migration speed difference imparting step in a separating unit.

6. An apparatus for forming a particle concentration difference in a dispersion liquid, comprising:
   pulse laser generating unit for generating a pulse laser;
   shock wave generating unit for generating a shock wave in a dispersion liquid having dispersed first particles having a first diameter and second particles having a second diameter larger than said first diameter, with said pulse laser generated by said pulse laser generating unit;
   migration speed difference imparting unit for migrating and accelerating said first particles at a first acceleration speed, and said second particles at a second acceleration speed higher than said first acceleration speed, by the shock wave generated by said shock wave generating unit; and
   separating unit for separating the first particles and the second particles accelerated and migrated by said migration speed difference imparting unit.

7. The method of particle detection according to claim 1, wherein
   said shock wave generating step includes a step of irradiating a predetermined focused position in said dispersion liquid with said pulse laser, and
   said detecting step includes a step of detecting said first or second particles passing through a predetermined observation position positioned apart from said predetermined focused position, at difference acceleration speeds generated by said shock wave generated at said focused position, with an observing pulse laser.

8. The method of particle detection according to claim 7, wherein
   said detecting step includes a step of irradiating said predetermined observation position with a pulse laser of said observing laser for detection.

9. The method of particle detection according to claim 7, wherein
   a wavelength of said shock wave generation laser is 1064 nm, and
   a wavelength of said observation laser is 355 nm.

10. The method of particle detection according to claim 7, wherein
    said detecting step is a step of detecting a refractive index, absorption degree, or fluorescent intensity of the particle.

11. The method of particle detection according to claim 7, wherein said second particles have a radius of 1 nm to 1 μm.

* * * * *